United States Patent [19]

Van Polen

[11] Patent Number: 4,543,097
[45] Date of Patent: Sep. 24, 1985

[54] OSTOMY BAG APPARATUS WITH SIDE WALL POCKET TO CONTAIN A DEODORANT MEMBER

[75] Inventor: Alta R. Van Polen, Rte. 2, Box 315H, Roscommon, Mich. 48653

[73] Assignees: Alta R. Van Polen; James F. Sartwell, both of Roscommon, Mich.

[21] Appl. No.: 438,370

[22] Filed: Nov. 1, 1982

[51] Int. Cl.⁴ .............................................. A61F 5/44
[52] U.S. Cl. .................................................. 604/333
[58] Field of Search .................... 422/5; 604/317, 327, 604/332–335, 337, 359; 239/36

[56] References Cited

U.S. PATENT DOCUMENTS

| | | | |
|---|---|---|---|
| 2,688,327 | 9/1954 | Borg | 604/333 |
| 4,173,979 | 11/1979 | Odis | 604/327 |
| 4,331,148 | 5/1982 | Steer et al. | 604/333 |
| 4,363,322 | 12/1982 | Andersson | 604/359 |
| 4,465,232 | 8/1984 | Field | 239/36 |

FOREIGN PATENT DOCUMENTS

| | | | |
|---|---|---|---|
| 1445658 | 6/1966 | France | 604/317 |
| 719063 | 11/1954 | United Kingdom | 604/333 |
| 2083760 | 3/1982 | United Kingdom | 604/333 |
| 2094153 | 9/1982 | United Kingdom | 604/333 |

Primary Examiner—C. Fred Rosenbaum
Assistant Examiner—J. L. Kruter
Attorney, Agent, or Firm—Michael L. Bauchan

[57] ABSTRACT

Ostomy bag apparatus is provided for covering an ostomy bag and providing a pocket in which a deodorizing member is positioned. The apparatus includes a non-irritating cloth cover that substantially encloses an ostomy bag and in which a pocket is formed by at least one fold in the cover to receive a deodorizing member impregnated by a volatile deodorant that is warmed and vaporized by body heat of the ostomate wearing the apparatus.

6 Claims, 3 Drawing Figures

OSTOMY BAG APPARATUS WITH SIDE WALL POCKET TO CONTAIN A DEODORANT MEMBER

BACKGROUND OF THE INVENTION

This invention relates to ostomy bag apparatus. The term "ostomy" refers to a surgical procedure in which a human or animal elimination system is re-routed to exit the body through a surgically created orifice called a "stoma" in the body surface. Two such surgical procedures are a "colostomy" in which part of the colon is removed and "ileostomy" in which part of the small intestine is removed.

A person who has undergone an ostomy procedure is an "ostomate" and wears an "ostomy bag" to collect waste material discharged through the stoma. Discharged waste material includes solids, liquids and gases generated by the digestive process. Ostomy bags commonly are vented to the atmosphere, thus reducing the rapid ostomy bag inflation that would result under the ostomate's clothing if an unvented bag were used.

A common concern of an ostomate is the socially undesirable odor emanating from an ostomy bag. Another common concern is the skin irritation which an ostomy bag may cause to the ostomate's skin. Ostomy bags are commonly made of a plastic material and are available from numerous sources, including E. R. Squibb & Sons, Inc. Cloth custom-fitted covers are sometimes worn over the plastic ostomy bag to minimize skin irritation and various apparatus has been designed to provide a deodorant intended to mask or neutralize odors emanating from an ostomy bag. Some such examples are: Riely, U.S. Pat. No. 3,690,320 issued Sept. 12, 1972 teaching a deodorizing packet inside a pouch; Kubach et al, U.S. Pat. No. 4,211,224 issued July 8, 1980 utilizing a vent which contains a deodorizing material; Bonfils, U.S. Pat. No. 3,439,677 utilizing a deodorant in a filter material; and Diack, U.S. Pat. No. 2,054,535 issued Sept. 15, 1936 utilizing a deodorizing cartridge. Some ostomates attempt to mask or neutralize odors simply by wearing a deodorant impregnated tissue or cloth looped over their belt so their body heat warms and vaporizes the deodorant.

It is an object of this invention therefore to provide apparatus for covering an ostomy bag with a non-irritating material and provide a pocket for receiving a deodorizing object in the ostomy bag cover; the deodorizing member including a volatile deodorant which is warmed and vaporized by body heat from the wearer.

The foregoing and other objects and advantages of the subject invention will become apparent from the accompanying drawing and description.

SUMMARY OF THE INVENTION

This invention relates to ostomy bag apparatus in which an ostomy bag cover is provided with a pocket for receiving a deodorizing material. The pocket is formed by at least one fold in the ostomy bag cover, which substantially encloses the ostomy bag. The deodorizing member includes a volatile deodorant which is warmed and vaporized by body heat of an ostomate wearing the apparatus.

DISCUSSION OF THE DRAWINGS

DESCRIPTION OF THE PREFERRED EMBODIMENT

Figure 1:
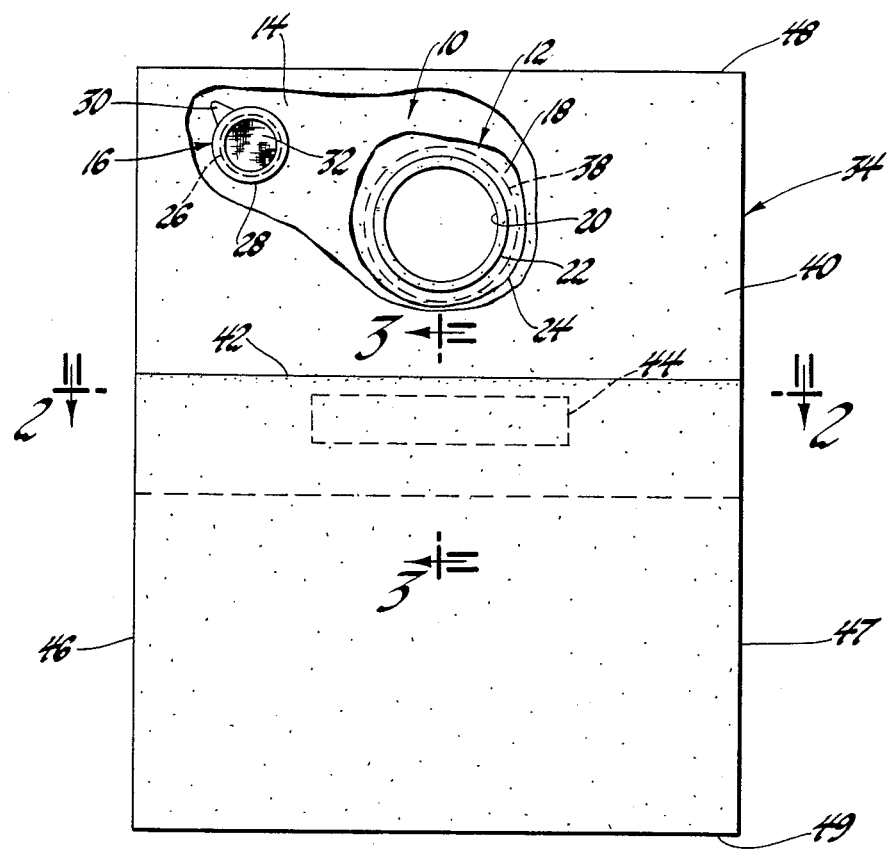
FIG. 1 is a plan view with parts removed of ostomy bag apparatus embodying the principles of the subject invention.

As shown in FIG. 1, a conventional ostomy bag 10 is illustrated which includes a sealed plastic envelope 12 having a front surface 14 on which is positioned a vent 16 and a back surface 18 adapted to be worn next to the body of an ostomate whose stoma is positioned in the center of an orifice 20 in the back surface 18 of the plastic envelope 12.

For purposes of illustration in FIG. 1 the back surface 18 of the plastic envelope 12 includes a semi-rigid plastic ring 22 which customarily is provided with an adhesive coating (not shown) on the side of the ring adjacent the ostomate's body for securely sealing the ring 22 to the ostomate's body to prevent waste material leakage and assure all waste products pass into the plastic envelope 12. To provide a simple illustration in FIG. 1 the front surface 14 is partially removed at 24 to show orifice 20. Persons versed in the art will appreciate that the front surface 14 is a solid plastic surface except where vent 16 is provided, which in the illustrated embodiment is of a conventional design having a rigid first ring 26 the middle of which opens to the interior of plastic envelope 12 and a second ring 28 provided with a tab 30 and a screen 32 of a suitable felt or other material which tends to be gas permeable but liquid non-permeable to facilitate venting gases from inside the plastic envelope 12 to the atmosphere.

The ostomy bag apparatus generally indicated at 34 which embodies the spirit of this invention includes a cloth back cover 36 in which an opening 38 is provided to accommodate the stoma of the ostomate wearing ostomy bag 10. The apparatus 34 also includes a front cover 40 in which a pocket 42 is provided to receive and support a deodorizing member 44. As shown in the drawings, back cover 36 and front cover 40 are substantially planar sheets which are preferably made of a non-irritating cloth material such as silk or cotton or synthetic substance which does not irritate human skin. In the illustrated embodiment the front cover 40 is secured to the back cover 36 at both sides 46 and 47 and at the top 48 so as to substantially surround the plastic envelope 12 and provide for the ostomy bag 10 supporting the front cover 40 and the back cover 36. The front cover 40 and the back cover 36 do not have to be fastened together at the bottom 49 and in practice it may be found easier to insert the ostomy bag 10 in the apparatus 34 if the bottom 34 is left open.

Figure 2:
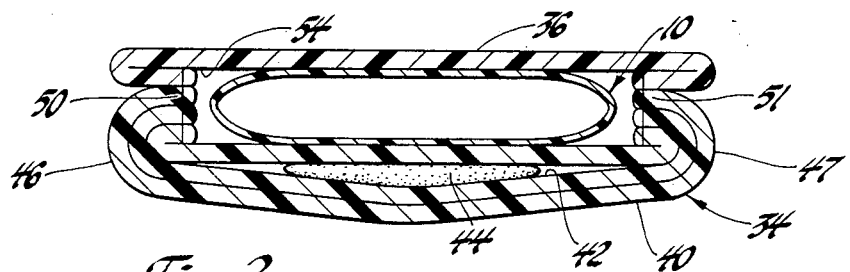
FIG. 2 is a sectional view of the apparatus in FIG. 1 taken along lines 2—2 and enlarged to show detail.

In FIG. 2 the cross section of the ostomy bag 10 and apparatus 34 is illustrated taken along the lines 2—2 in FIG. 1. In FIG. 2 the structure of the apparatus 34 is enlarged to show detail. As shown in FIG. 2, in the illustrated embodiment the apparatus 34 is constructed by folding the back cover 36 and front cover 40 and sewing them together adjacent sides 46 and 47 by stitches 50 and 51. Persons versed in the art will appreciate that other means can be provided for fastening back cover 36 to front cover 40.

Figure 3:
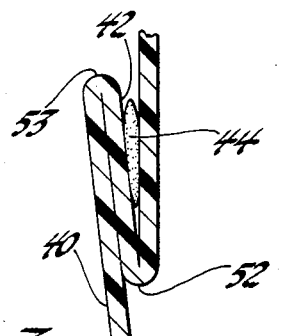
FIG. 3 is a partial sectional view of the apparatus in FIG. 1 taken along lines 3—3 and enlarged to show detail.

In the illustrated embodiment the pocket 42 is formed by two folds 52 and 53 most clearly shown in FIG. 3, which is a partial cross section view of the front cover 40, deodorizing member 44, and pocket 42. Since it is desired to mask or neutralize odors emanating through screen 32 the pocket 42 in the illustrated embodiment is positioned in the upper part of front cover 40. Persons versed in the art will appreciate that pocket 42 can be positioned near the top 48 or the bottom 49 if such would be preferred and by positioning it at the bottom 49 only fold 52 would be required to form pocket 42 in front cover 40.

To use the apparatus 34 the ostomate inserts the ostomy bag 10 through opening 38 so the ring 22 is aligned with the opening 38 and the ostomy bag 10 is fully opened. The ostomate can reach through the open bottom 49 to smooth ostomy bag 10 within space 54 provided between back cover 36 and front cover 40. The ostomate then inserts the deodorizing member 44 in the pocket 42 and ring 22 is attached to the ostomate's skin for use of the ostomy bag in the normal manner. Since back cover 36 keeps most of ostomy bag 10 away from the skin of the ostomate irritation sometimes caused by plastic materials used in envelope 12 is minimized.

The pocket 42 is provided in front cover 40 in the preferred embodiment to facilitate pocket 42 access. The deodorizing member 44 which the ostomate chooses to use will depend upon personal preference of the ostomate. In the preferred embodiment the deodorizing member 44 is a tissue permeated with a volatile deodorant commonly marketed to add freshness to clothing by placing it in a conventional clothes dryer of the type in common usage in the United States. Bounce is a trademark of such a tissue in common usage. The tissue is flexible and does not bulge as the apparatus 34 moves with the ostomate's body. The volatile deodorant with which the tissue is impregnated is heat responsive so the ostomate's body heat while wearing the apparatus 34 warms and vaporizes the deodorant to mask the odor which is unavoidable in using an ostomy bag 10. Other deodorizing members 44 which may be in solid form or may provide a different aroma can be used according to the preference of the ostomate.

As persons versed in the art will appreciate, the pocket 42 can be formed in the back cover 36 and may be positioned in a vertical orientation rather than horizontal orientation as illustrated without departing from the spirit of the invention. Persons versed in the art will appreciate that various other modifications may be made of the subject apparatus without departing from the spirit of the invention.

What is claimed is:

1. An ostomy bag cover comprising, in combination an ostomy bag enclosure which includes a first section and a second section which are attached together so as to form an ostomy bag enclosure which is adapted to substantially enclose an ostomy bag between said sections and be supported by an ostomy bag, fold means in at least one of said sections so as to form a pocket of a continuous fold of one of said sections which forms the ostomy bag cover and means for retaining said fold means in said one section whereby a deodorizing member may be inserted in said pocket so as to be supported by said pocket.

2. The ostomy bag cover of claim 1 in combination with a deodorizing member in said fold means and supported by said fold means.

3. The ostomy bag cover of claim 1 in combination with a deodorizing member positioned in said fold means and supported by said fold means, said deodorizing member including a support material and a heat responsive volatile deodorant whereby body heat generated by an ostomate while wearing said ostomy bag cover warms and vaporizes said deodorant.

4. The ostomy bag cover of claim 1 in which said fold means forms an exterior pocket.

5. The ostomy bag cover of claim 1 in which said first section is adapted to keep at least part of an ostomy bag from contacting the body of an ostomate and said second section is secured to said first section and positioned on the side of said first section opposite said body of said ostomate, said fold means being in said second section so as to form an exterior pocket in said second section for receiving a deodorizing member.

6. The ostomy bag cover of claim 1 in which said first section is adapted to keep at least part of an ostomy bag from contacting the body of an ostomate and said second section is secured to said first section and positioned on the side of said first section opposite said body of said ostomate, said fold means being in said second section so as to form an exterior pocket in said second section, and a deodorizing member positioned in said exterior pocket in said second section, said deodorizing member including a support material and a heat responsive volatile deodorant whereby body heat generated by said ostomate while wearing said ostomy bag cover warms and vaporizes said deodorant.

* * * * *